(12) United States Patent
Lewallen et al.

(10) Patent No.: US 10,716,677 B2
(45) Date of Patent: Jul. 21, 2020

(54) PROSTHESIS AND METHODS INCLUDING ANATOMICALLY POSITIONED HOLES

(71) Applicant: Zimmer, Inc., Warsaw, IN (US)

(72) Inventors: David Lewallen, Rochester, MN (US); Rafael Sierra, Rochester, MN (US); Jacob Macke, Warsaw, IN (US); Aaron P. Smith, Warsaw, IN (US); Robert D. Krebs, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 93 days.

(21) Appl. No.: 15/988,777

(22) Filed: May 24, 2018

(65) Prior Publication Data
US 2018/0344466 A1    Dec. 6, 2018

Related U.S. Application Data

(60) Provisional application No. 62/512,888, filed on May 31, 2017.

(51) Int. Cl.
*A61F 2/34* (2006.01)
*A61F 2/46* (2006.01)
*A61F 2/30* (2006.01)

(52) U.S. Cl.
CPC ............ *A61F 2/34* (2013.01); *A61F 2/30767* (2013.01); *A61F 2/4609* (2013.01); *A61F 2002/30332* (2013.01); *A61F 2002/30367* (2013.01); *A61F 2002/30617* (2013.01); *A61F 2002/30822* (2013.01); *A61F 2002/3401* (2013.01); *A61F 2002/3403* (2013.01); *A61F 2002/3469* (2013.01); *A61F 2220/0025* (2013.01); *A61F 2250/0097* (2013.01)

(58) Field of Classification Search
CPC .. A61F 2/34; A61F 2/4609; A61F 2002/3401; A61F 2002/3469; A61F 2002/30617; A61F 2250/0097
See application file for complete search history.

(56) References Cited

U.S. PATENT DOCUMENTS

| | | | | |
|---|---|---|---|---|
| 2012/0179270 A1* | 7/2012 | Nevins | ........................ | A61F 2/34 623/22.35 |
| 2012/0289965 A1* | 11/2012 | Gelaude | ................. | A61B 17/15 606/87 |
| 2013/0035766 A1* | 2/2013 | Meridew | .................... | A61F 2/34 623/22.21 |
| 2015/0313724 A1* | 11/2015 | Jackson, III | ........... | A61B 90/39 623/22.12 |
| 2019/0053915 A1* | 2/2019 | Macke | .................... | A61B 34/10 |

* cited by examiner

*Primary Examiner* — Thomas Sweet
*Assistant Examiner* — Javier G Blanco
(74) *Attorney, Agent, or Firm* — Schwegman Lundberg & Woessner, P.A.

(57) ABSTRACT

A method of anatomically positioning screw holes in an acetabular implant that can be used in surgery, such as a total hip arthroplasty. In some examples the method can be used to position holes in a shell of the implant. The method can include, for example, obtaining anatomic data including data defining an arch of bone behind an acetabulum of the living being, the arch of bone extending from a superior anterior portion to an inferior posterior portion of the acetabulum. The method can further include positioning a first series of holes along a first arched line within the acetabular shell, the first arched line determined based on the anatomic data for the arch of bone proximate the acetabulum of the living being.

17 Claims, 12 Drawing Sheets

PROSTHESIS AND METHODS INCLUDING ANATOMICALLY POSITIONED HOLES

CLAIM OF PRIORITY

This application claims the benefit of U.S. Provisional Patent Application Ser. No. 62/512,888, filed on May 31, 2017, the benefit of priority of which is claimed hereby, and which is incorporated by reference herein in its entirety.

TECHNICAL FIELD

This document pertains generally, but not by way of limitation, to orthopedic devices, and, more particularly, to prosthesis such as acetabular implants including shells and cups used in total hip arthroplasty.

BACKGROUND

A total hip arthroplasty (THA) procedure can be performed to repair a diseased or damaged hip joint and replace it with a hip prosthesis. Sometimes, as with any other mechanical device, a total hip replacement can be subject to various forms of mechanical or biological issues. When issues occur, a reoperation of the hip prosthesis can be necessary to resolve the issues. Such a reoperation of a THA is called a revision THA. This is usually done several years after the original implantation and is more common in patients who had the initial THA performed at a young age and the patient chose to have a very active physical lifestyle.

One of the challenges of a revision THA is how to securely implant the hip prosthesis, and in particular, how to securely implant an acetabular revision shell of the hip prosthesis into the remaining bone of the patient, especially in the presence of poor bone quality or bone loss.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

Figure 1A:
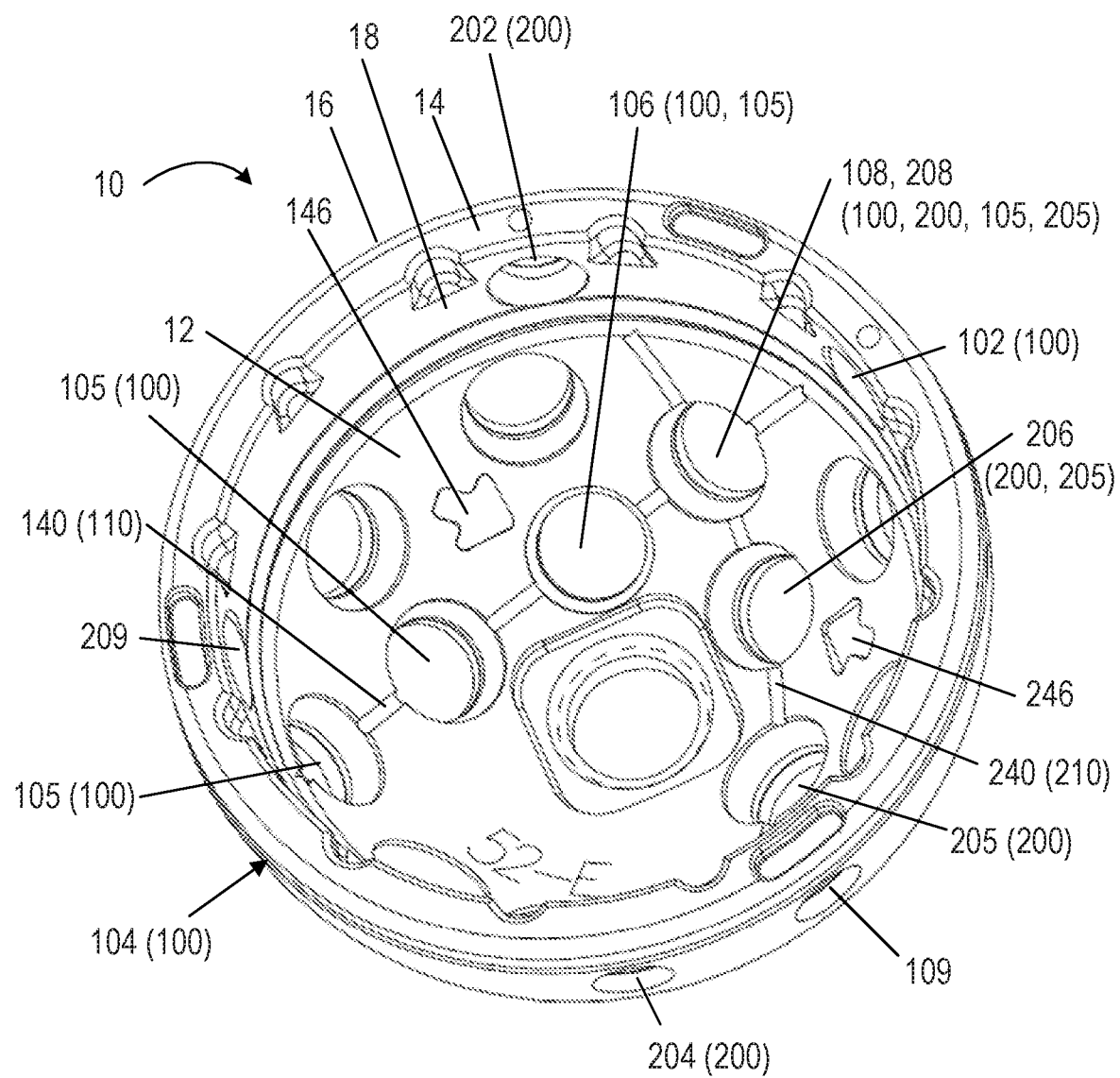
FIG. 1A is a perspective view of an illustrative shell, in accordance with at least one example.

As discussed above, one of the challenges of a revision total hip arthroplasty (THA) is how to securely implant the hip prosthesis, and in particular an acetabular revision shell of the hip prosthesis into the remaining bone of the patient, especially in the presence of poor bone quality or bone loss.

When using conventional acetabular revision shells, surgeons have to mentally align clusters or randomly oriented screw holes with the bone to which the shell is to be secured. The goal of the surgeon is to select, from the screw holes available in the shell, the best options for screwing the shell into the available bone. When the screw holes are randomly placed or clustered in the shell, placing screws through the available holes to try and match up with the available bone does not always produce the desired results.

Improved acetabular shells and methods for positioning holes in acetabular shells are described herein. An acetabular shell with optimized hole positioning based on anatomical arches have been found by the inventors to solve the problem of providing sufficient screw fixation in revision total hip arthroplasty (THA) when many screws are required to achieve biological fixation of the shell. Conventional shells and particularly shells with a hard bearing taper are not able to achieve optimal screw hole locations in order to place screws in the remaining bone during revision. The disclosure herein applied to shells, can also be applied to cups, such as a cup inserted into a shell that acts as a liner, or a cup directly implanted without a shell. While described in relation to revision THA, the prosthesis and methods may also be applied to non-revision, or primary THA surgeries and prosthesis.

The devices and methods disclosed herein align a series of holes in an acetabular shell of a hip prosthesis with a desirable arch of bone. More specifically, the acetabular shell includes anatomically positioned holes that are arranged along an arch in the shell that match up with an arch of the hip bone. As a result the acetabular shell is more securely fixed to the bone. In addition, the devices, systems and methods eliminate the mental aligning that the surgeon has to do when implanting conventional shells that lack the anatomically aligned and positioned screw holes of this disclosure.

The shell can also include markers that indicate to the surgeon the preferred hole selection and markers to aid in alignment of a single acetabular shell with either a right acetabulum or a left acetabulum. Because the alignment and positioning is made more clear and straightforward over conventional acetabular shells, the quality of the implantation can be made more reliable and the operating room time can be reduced.

While the term "hole" in this disclosure is generally associated with a screw hole, it is not necessarily limited to holes that can only be used with screws. Other suitable types of fasteners besides screws can be inserted through the holes disclosed herein.

Figure 1B:
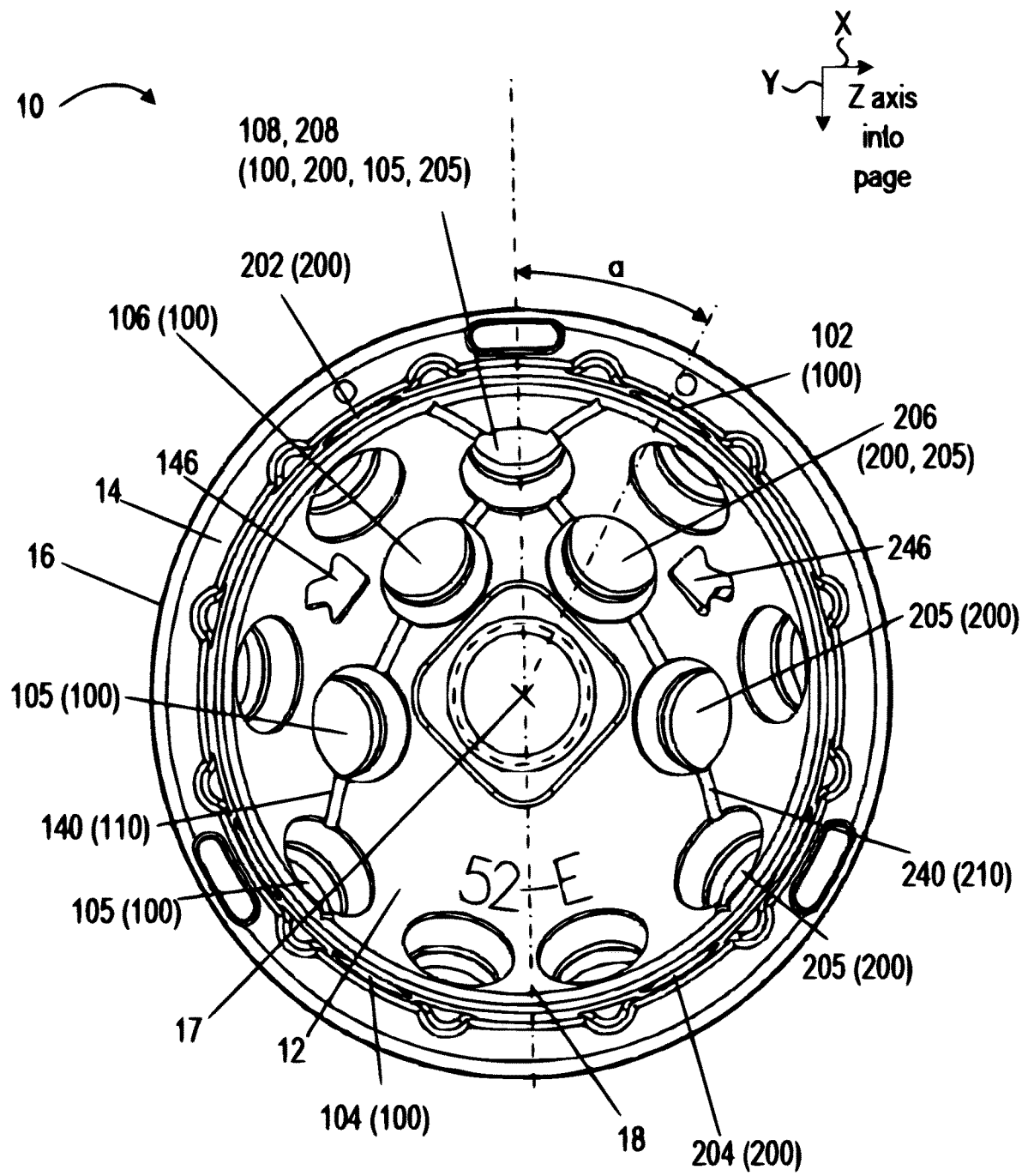
FIG. 1B is a front view of the illustrative shell of FIG. 1A, in accordance with at least one example.
Figure 1C:
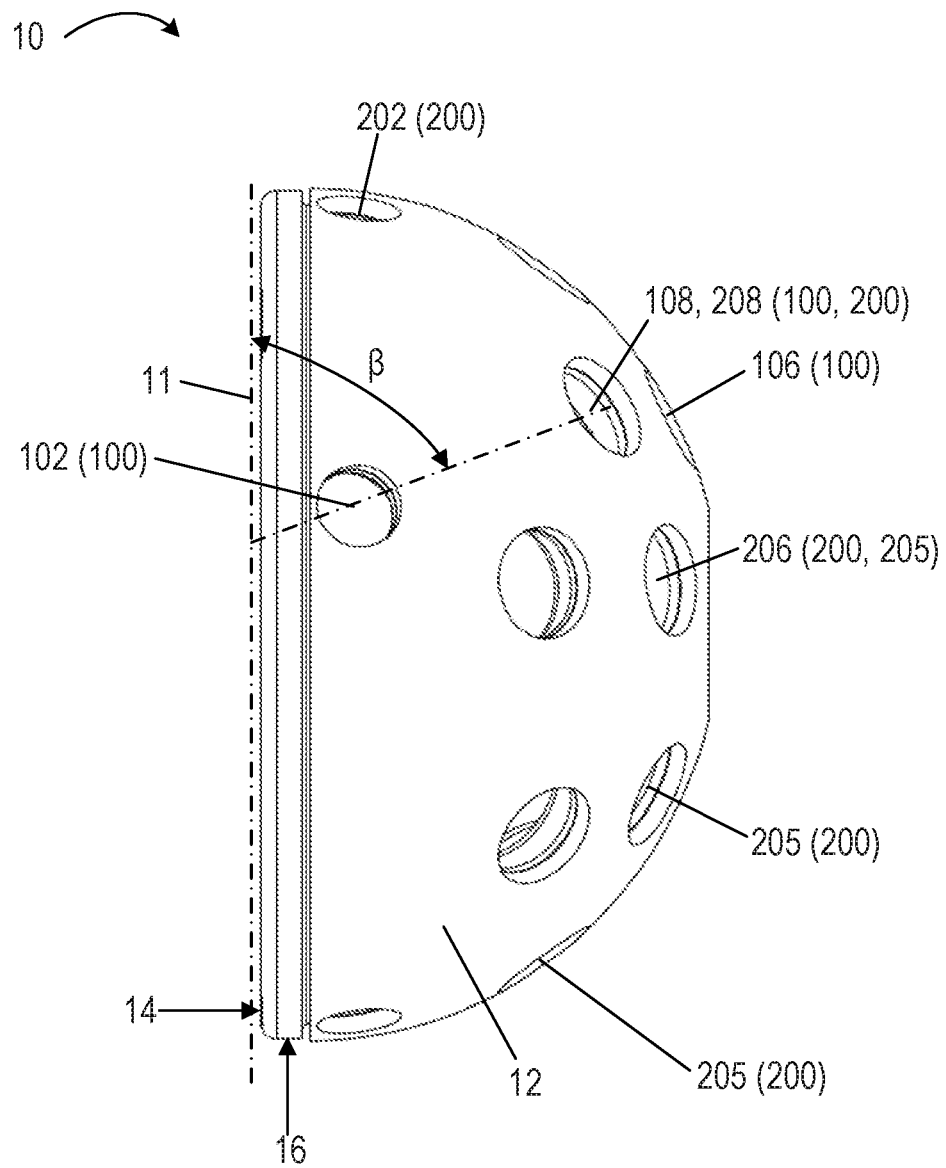
FIG. 1C is side view of the illustrative shell of FIG. 1A, in accordance with at least one example.
Figure 1D:
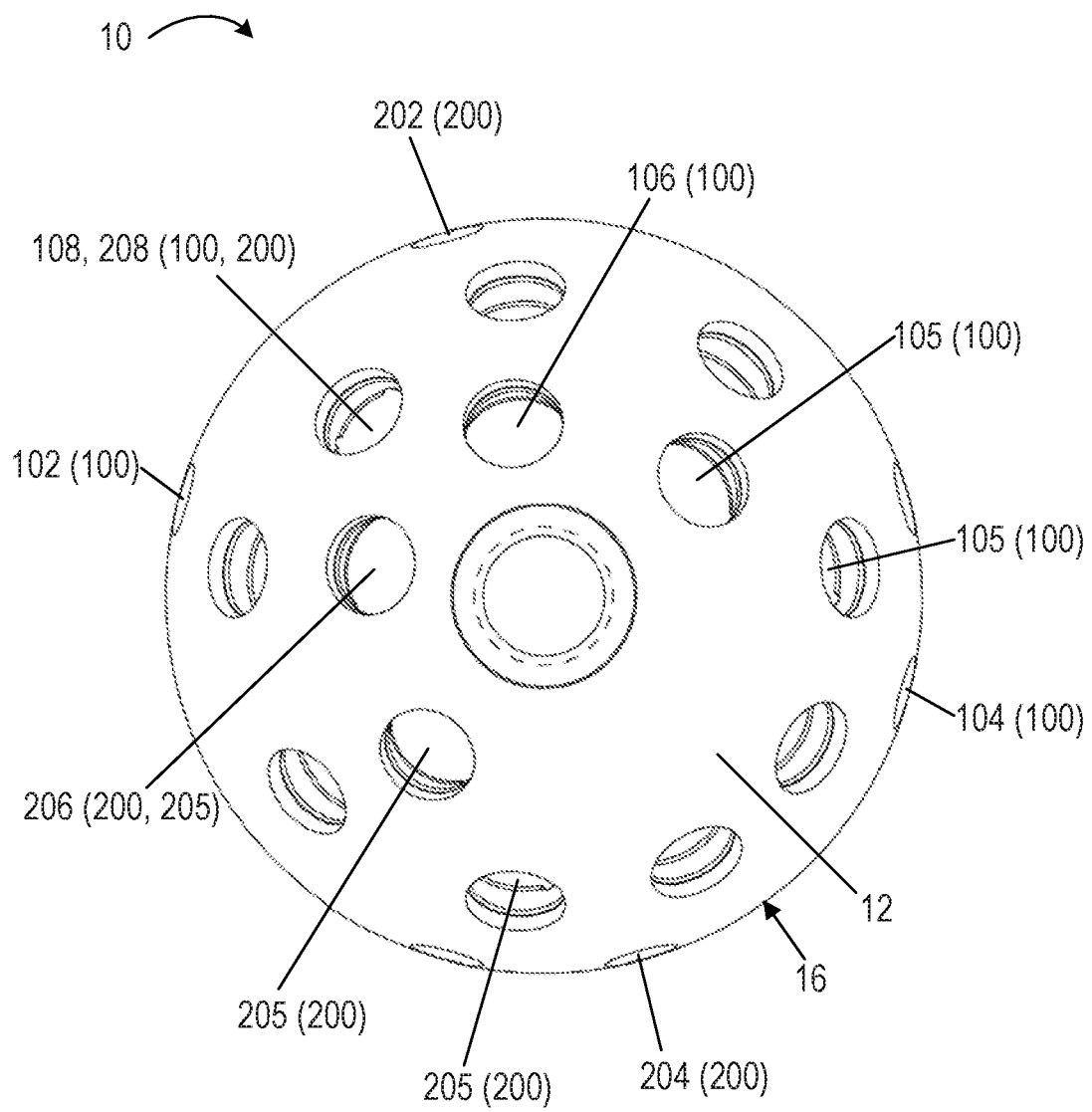
FIG. 1D is a rear view of the illustrative shell of FIG. 1A, in accordance with at least one example.

FIG. 1A is a perspective view of an illustrative acetabular shell 10, hereinafter shell 10, having anatomically positioned screw holes (e.g., any of 100) in accordance with at least one example. FIGS. 1B, 1C and 1D are front, side and rear views of the illustrative shell 10 of FIG. 1A.

Figure 2A:
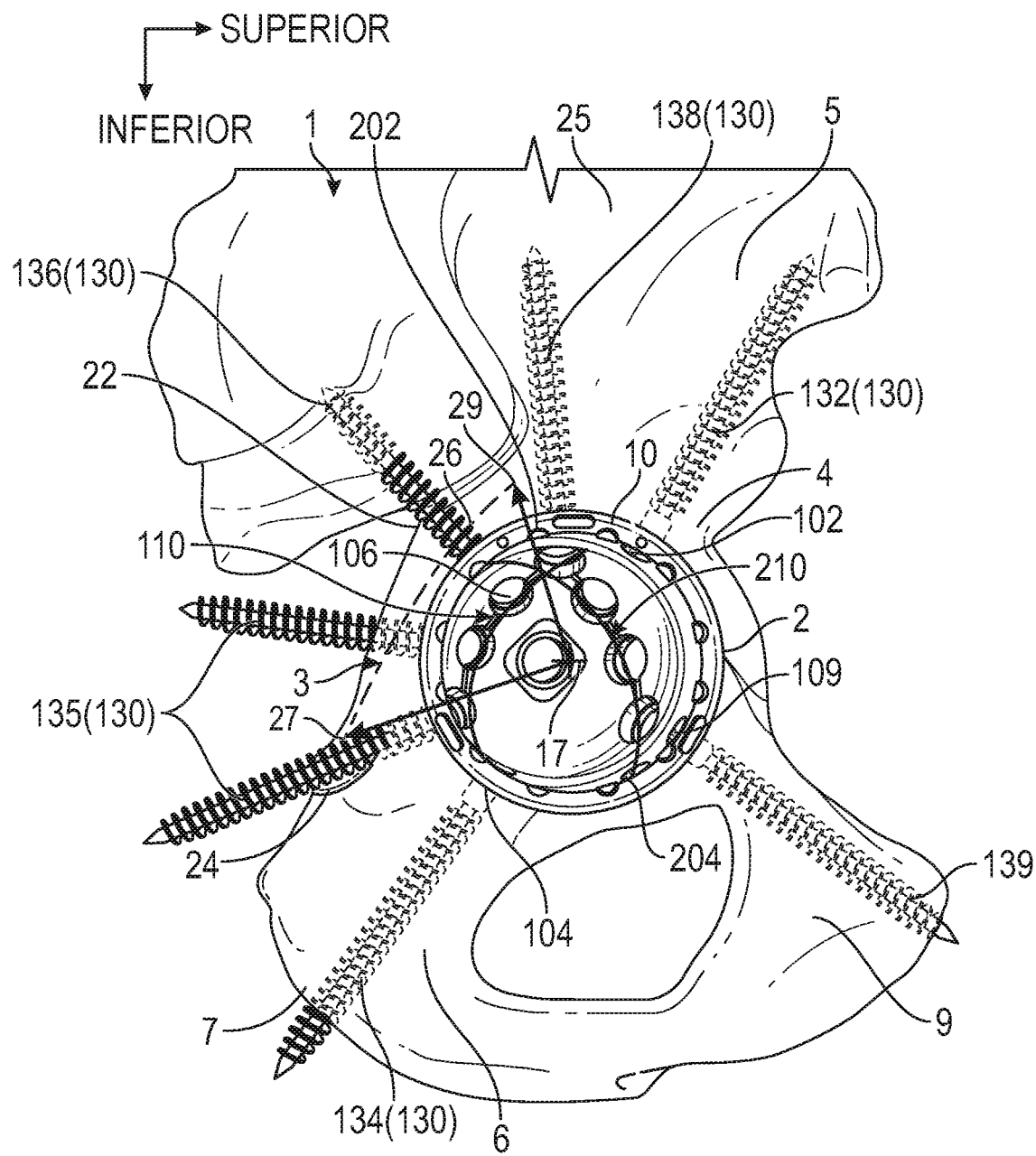
FIG. 2A is an anterior view of an illustrative shell similar to the shell of FIG. 1A, implanted into an acetabulum of a left hip bone with fixation screws, in accordance with at least one example.
Figure 2B:
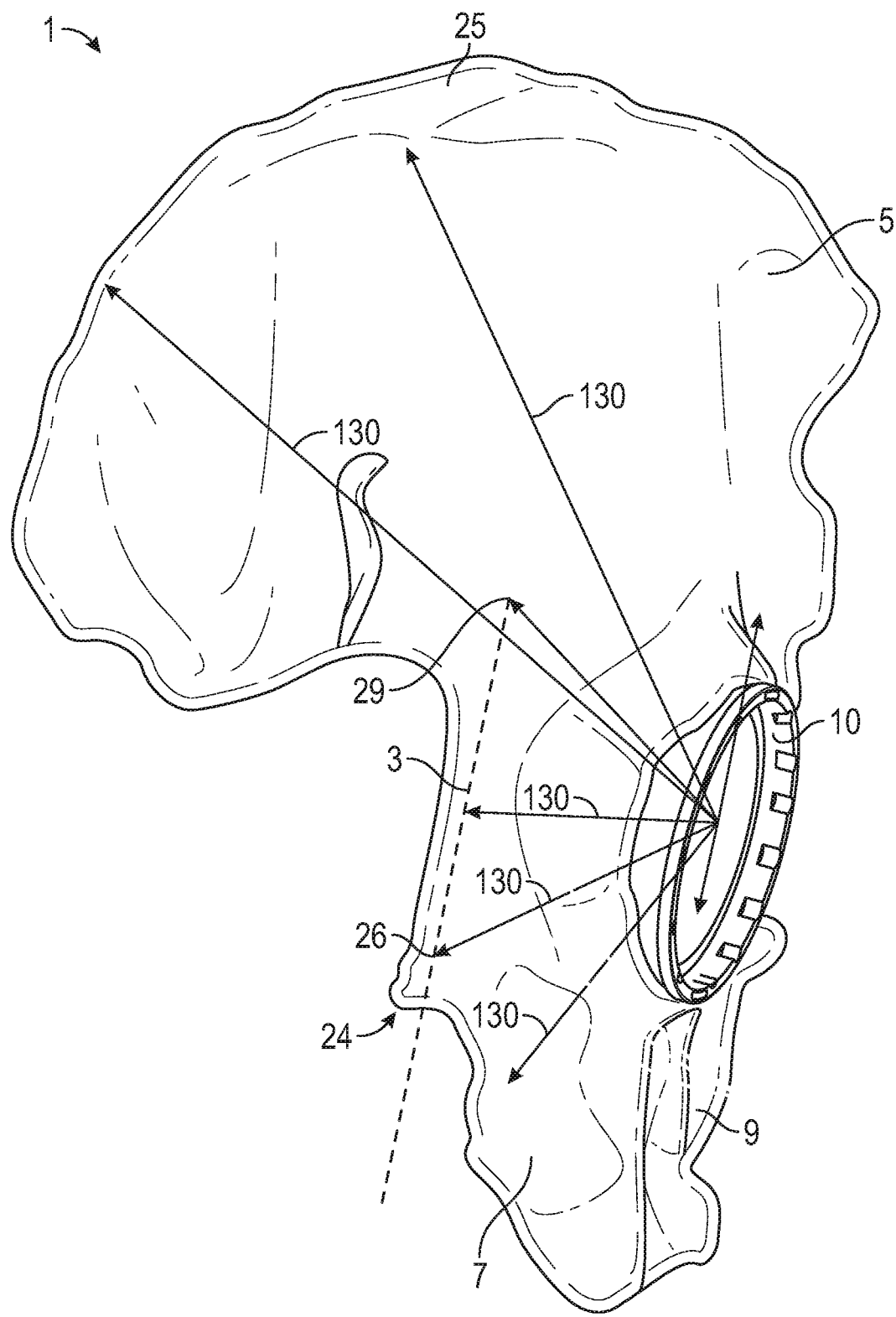
FIG. 2B is a lateral view of a hip bone and the illustrative shell of FIG. 2A showing the direction of the implanted screws extending from a center of the shell into the bone, in accordance with at least one example.
Figure 2C:
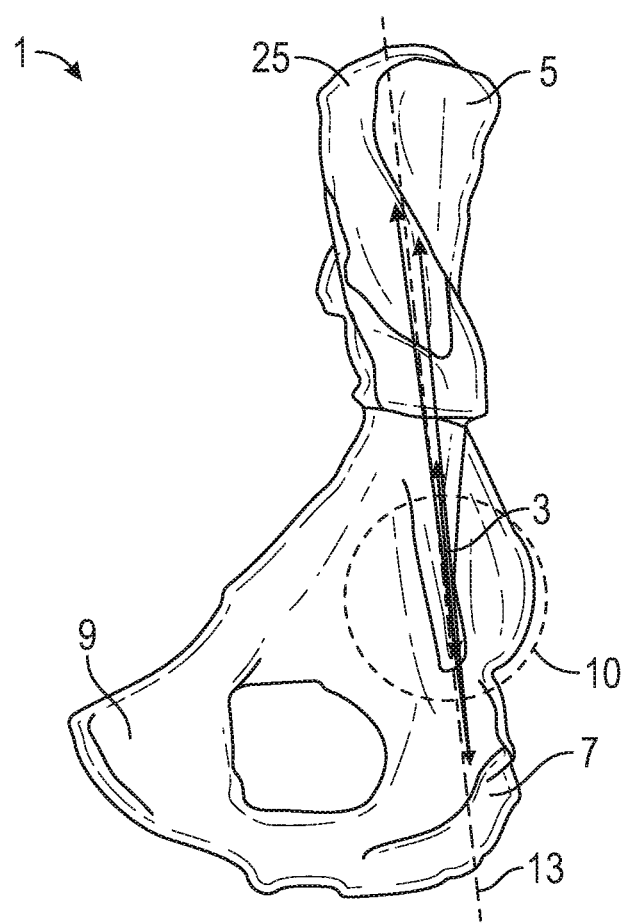
FIG. 2C is a posterior view of a hip bone, showing the position of the illustrative shell of FIG. 2A and the direction of the implanted screws as shown in FIG. 2B, in accordance with at least one example.

FIGS. 2A-2C show how the illustrative shell 10 is oriented in a hip bone 1. FIG. 2A shows an anterior view of the illustrative shell 10 and a plurality of fixation screws 130 shown implanted into an acetabulum of a left hip bone 1. FIG. 2B is a lateral view of the hip bone and the illustrative shell of FIG. 2A showing the direction of the implanted screws extending from a center of the shell into the bone. FIG. 2C is a posterior view of the hip bone and the illustrative shell of FIG. 2A (shown in hidden line), along with the direction of the implanted screws of FIG. 2B.

As perhaps best understood with reference to FIGS. 1A and 1B, the example shell 10 can include a generally hemispherical shaped dome 12 and a rim 16 along a face 14 of the shell 10. In some examples, the dome 12 can be described as terminating at the face 14 of the shell 10. In addition, the rim 16 can be described as extending around the circumference of the shell 10. The shape of the shell 10 can be tailored for implantation in an acetabulum 2 of a living being.

To facilitate an improved attachment of the shell 10 to the hip bone 1, the inventors have recognized a solution of anatomically positioning of screw holes (e.g., any of 100) in the shell 10 to correspond to an arch of bone 3 of the hip bone 1 (FIG. 2A-2C). The shells and methods in this disclosure include a description of different types of holes, of which any may be positioned along an arch of bone. In some examples, only some of the holes described are located along the arch of bone.

With reference to FIGS. 1A and 1B, and with the support of FIG. 2A, a bearing taper 18 can be included at or near the rim 16 (e.g., proximate the rim). In some embodiments, the bearing taper 18 can include a first hole 102 (best viewed in FIG. 1A, but can also be viewed in FIG. 1B) and a second hole 104 (best viewed in FIG. 1B). The first hole 102 and the second hole 104 can, but are not required, to generally oppose one another.

In some examples, the first and second holes 102, 104 can be located at opposite ends of a first arched line 110 (shown in FIG. 2A). In FIG. 2A, the first arched line is depicted as line 110. In FIGS. 1A and 1B, a marker that generally corresponds to the first arched line 110, is depicted as a first elongate marker 140. The first elongate marker 140 can be described as approximating the location of this first arched line 110. The first elongate marker 140 will be described in further detail later in this disclosure, but it is introduced now because the location of the first elongate marker 140 is helpful in understanding the location of the first arched line 110.

As previously described, the first and second holes 102, 104 can generally oppose one another. For example, the first and second holes 102, 104 can be at or about 180 degrees opposite one another along the circumference of the shell 10 such that the first and second holes 102, 104 face each other. In some examples, the first and second holes 102, 104 can oppose one another such that they are separated around the circumference of the shell 10 within a range of 150-210 degrees. In another embodiment, the first and second holes 102, 104 can be separated around the circumference of the shell 10 within a range of 165-195 degrees apart.

In some examples the first and second holes 102, 104 can be located outside of the bearing taper 18, in another part of the shell 10, such as below or adjacent the bearing taper 18. In at least one example, the first and second holes 102, 104 can be located partially or completely outside of the bearing taper 18.

Also shown in the example of FIGS. 1A and 1B, a first series of intermediate holes 105 can be located in the dome 12 of the shell 10 below the bearing taper 18. In some examples, and as shown in the present example, the first series of intermediate holes 105 can be located in between the first hole 102 and the second hole 104. Any of the first hole 102, the second hole 104, and one or more of the intermediate holes 105 can, together, form a first series of holes 100 positioned along the first arched line 110 (first arched line shown in FIG. 2A, or along elongate marker 140 in FIGS. 1A and 1B).

In the example shown, the first arched line 110 can be arranged to extend along the dome 12 of the shell 10 from the first hole 102 to the second hole 104 and including all of the intermediate holes 105.

In some embodiments the first arched line can extend from any one the first series of holes 100, to any other one of the first series of holes 100. In some embodiments, the first series of holes located along the first arched line does not include the first hole 102 and/or the second hole 104 being located along the first arched line 110. In such an example, if the first and/or second hole 102, 104 are provided, they may be located elsewhere on the shell 10 in a location that is not positioned along the first arched line 110, and instead can be aligned with another portion of the hip bone 1.

As previously described, FIG. 2A shows a view of the shell 10 implanted in a hip bone 1. Reference to FIGS. 2B and 2C, together with FIG. 2A, provide a further understanding of the arrangement of the first series of holes 100 in the shell 10 relative to the anatomy of the bone 1.

As shown in FIG. 2A, the first arched line 110 can correspond to (e.g., be aligned with) an arch of bone 3 behind (e.g., proximate) a right acetabulum 2 of the living being. The arch or bone 3 is also generally labeled in FIGS. 2B and 2C. In some examples, the arch of bone 3 of the right acetabulum 2 can extend from a superior anterior portion 4 to an inferior posterior portion 6 of the right acetabulum 2. Because the first series of holes 100 can be arranged along the first arched line 110, and the first arched line 110 can correspond to the arch of bone 3 behind a right acetabulum 2, the first series of holes 100 can be beneficially positioned to correspond to the arch of bone 3 behind the right acetabulum 2. This arrangement of the first series of holes 100 provides anatomically positioned holes that the surgeon can rely on for alignment and fixation of the shell 10 to the right acetabulum 2 and surrounding bone 1.

In addition to the anatomical positioning depicted in FIGS. 1A-1D and 2A-2C, FIGS. 2D-2G show an example of how the anatomical positioning of the first series of holes 100 in a hip bone 1 is geometrically incorporated in the shell 10. In general, the location of the first arched line 110 can be geometrically described as being located in the shell at a rotation angle α and a down angle β. First, the rotation angle α will be described, followed by the down angle β.

Figure 2D:
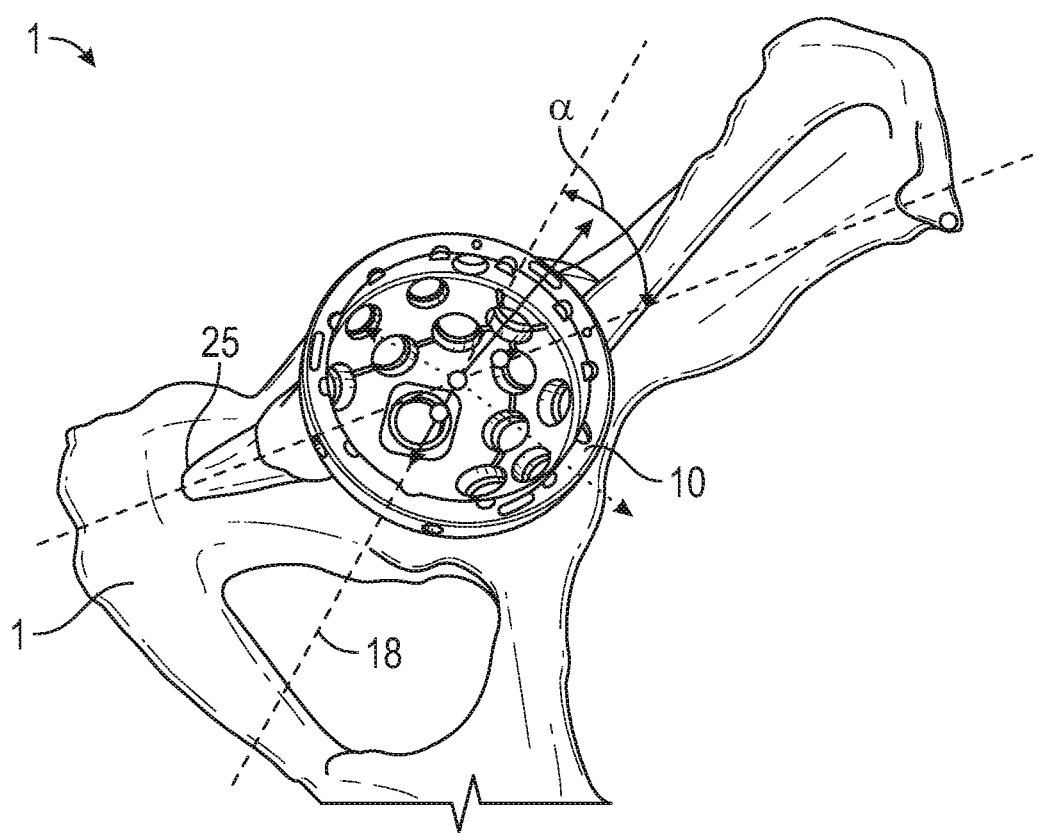
FIG. 2D shows an illustrative example of determining a rotation angle for anatomically positioning holes in the shell of FIG. 2A, in accordance with at least one example.
Figure 2E:
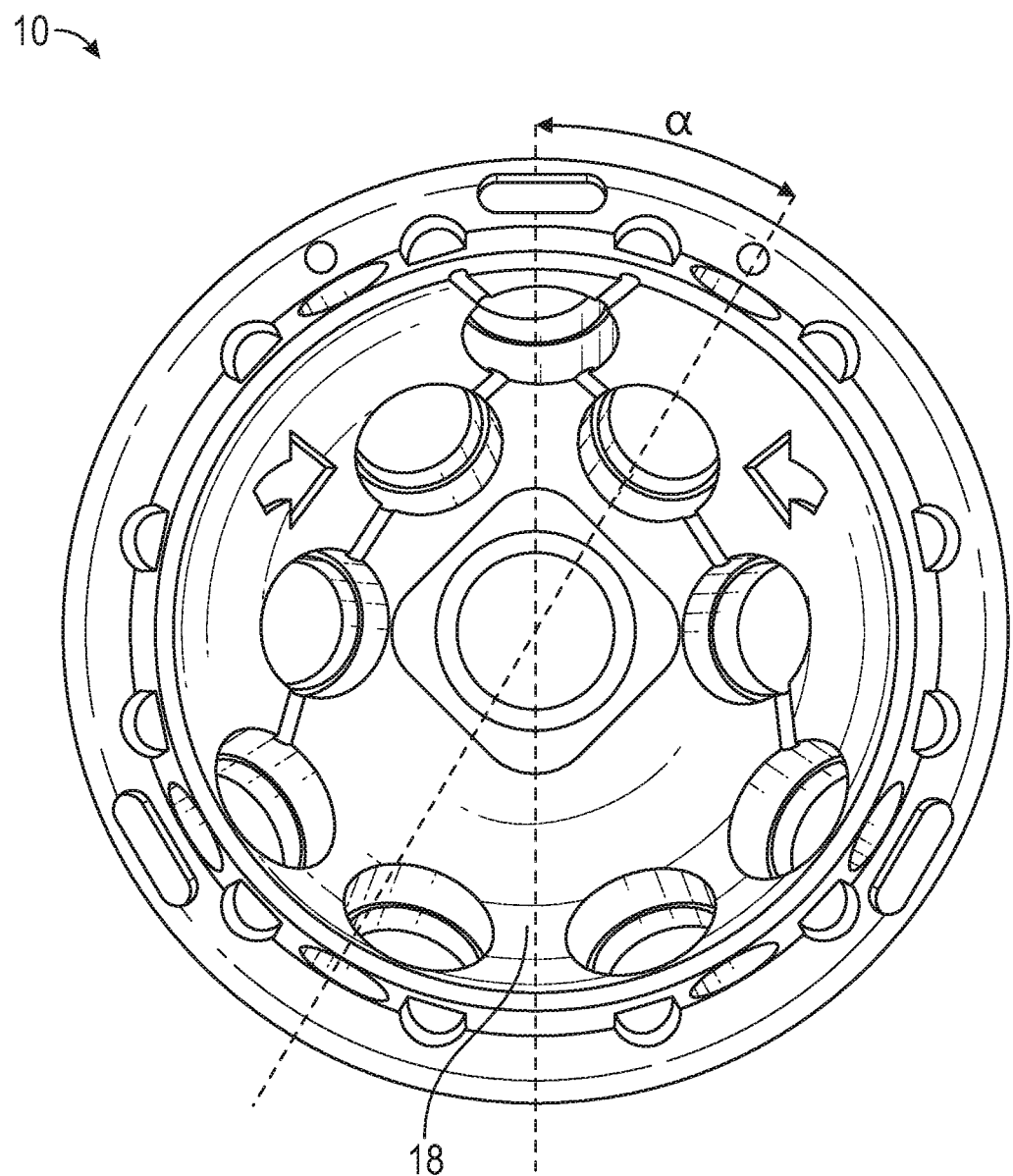
FIG. 2E shows how the rotation angle α that was determined in FIG. 2D, is implemented in the shell of FIG. 2A, in accordance with at least on example.

FIG. 2D shows an illustrative example of how the rotation angle α is determined for anatomically positioning holes in the shell 10. FIG. 2E shows how rotation angle α that was determined in FIG. 2D is incorporated in the shell 10, in accordance with at least on example.

As shown in FIG. 2D, the rotation angle α is the angle between the centerline 18 of the shell 10 and a line extending from the center 17 of the shell 10 through the ischial spine 24 of the hip bone 1, when the shell 10 is properly oriented in the hip bone.

For example, the first arched line 110 can be positioned at the rotation angle α about 30 degrees rotated off of the center line 18 extending through a center 17 of the shell 10, in either a clockwise or counter-clockwise direction (FIGS. 2D, 2E and also FIG. 1B). In other words, the first hole 102 can be oriented at a rotation angle α of about 30 degrees off of the center 17. In some examples, the rotation angle α can be about 20 to 40 degrees off of the center 17. In some embodiments the rotation angle α can be about 20 to 40 degrees off of another point on the center line 18.

In some examples, the rotation angle α can be implemented with respect to other reference points, and other values for the rotation angle α can be used. In some examples, the rotation angle α can be determined relevant to other references points on or near the center line 18. In some examples, the rotation angle α can be determined relevant to reference points other than the center 17 or centerline 18.

Figure 2F:
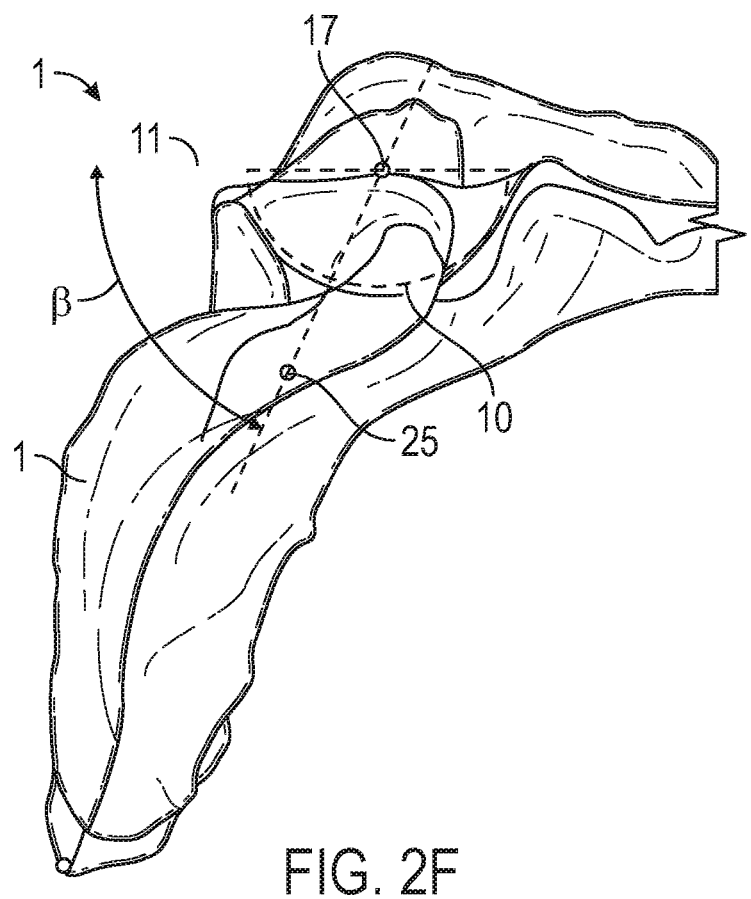
FIG. 2F shows an illustrative example of determining a down angle for anatomically positioning holes in the shell of FIG. 2A, in accordance with at least one example.
Figure 2G:
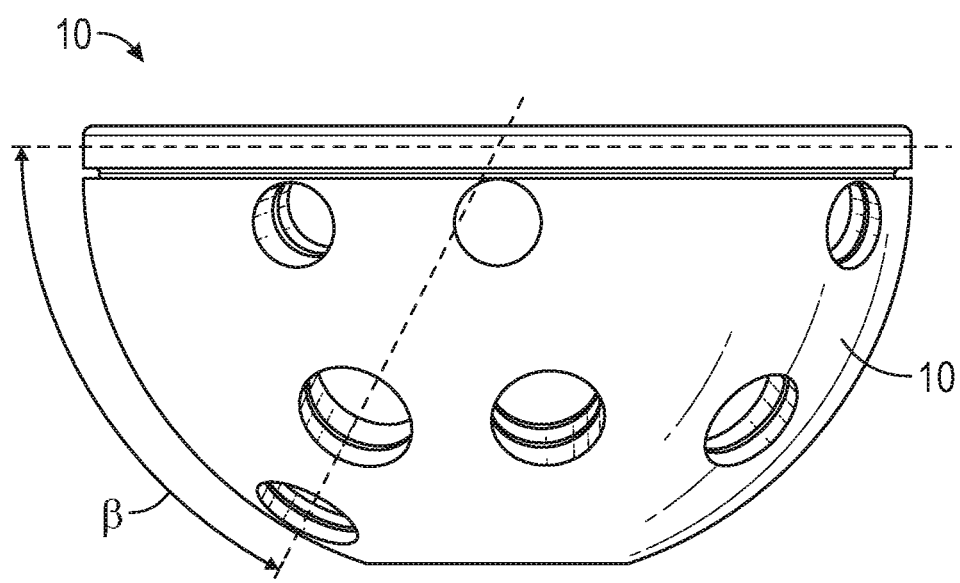
FIG. 2G shows how the down angle β that was determined in FIG. 2F, is implemented in the shell of FIG. 2A, in accordance with at least one example.

With regard to the down angle β, FIG. 2F shows an illustrative example of how the down angle β for anatomically positioning holes 100 in a shell 10 is determined. FIG. 2G shows how the down angle β that was determined in FIG. 2F is implemented in the shell 10, in accordance with at least one example. The down angle β can be described as the angle between the first plane 11 that is parallel (e.g., generally parallel or within ±10 degrees) to the face 14 of the shell 10, and a line from the center of the shell intersecting the ischial spine 24.

In some examples the down angle β can be about 65 degrees down from level with the face 14 of the shell 10 (FIGS. 2F, 2G and FIG. 1C). In some examples, the down angle β can range between 40 to 75 degrees depending on the geometry of the first arched line 110.

Looking again to FIGS. 1A, 1B and 2A, depending on the geometry of the arch of bone 3 that is used to determine the geometry of the first arched line 110, the opposing relationship between the first and second holes 102, 104 may not be exactly 180 degrees opposite one another. As previously described, variations are possible. Some reasons for variation can include variations due to anatomical geometry as previously discussed, and also manufacturing capabilities and tolerances, as well as the need to ensure adequate tool access to during surgery.

In some examples, the first arched line 110 can be based on anatomic data from an anatomic database. In some examples, the anatomic data can represent data pertaining to a subset of a living being population that is obtained from the anatomic database. An anatomic database is a source of anatomical dimensions that can include anatomic dimensions for living beings of different sizes. In some examples, the first arched line 110 is based on anatomic data, not from an anatomic database, but can be derived from anatomic data for a particular living being, such as anatomic data obtained for a particular living being during preoperative imaging procedures. Preoperative images can be used to build a virtual model of the applicable bone 1 (e.g., acetabulum 2), which can then be used to determine locations of the first arched line 110 and a series of holes 100 that corresponds to the first arched line 110.

While the first arched line 110 (FIG. 2A) can provide features for attaching the shell 10 to right acetabulum 2, a corresponding second arched line 210 (FIG. 2A) can include features for attaching the shell 10 to a left acetabulum (e.g., mirror image of FIG. 2A). In FIGS. 1A and 1B, the second arched line 210 can be described as extending along a second elongate marker. All of the features provided in relation to the first arched line 110, including the first and second holes 102, 104, the first series of intermediate holes 105 can be applied to the second arched line 210.

For example, similar to the first and second holes 102, 104 that can provide attachment to a right acetabulum 2, a third hole 202 and a fourth hole 204 generally opposing one another can be provided in, adjacent or below the bearing taper 18 for attachment to a left acetabulum 2 of the living being (e.g., mirror image of FIG. 2A). The third and fourth holes 202, 204 can incorporate all the features described with respect to the first and second holes 102, 104, with the third and fourth holes 202, 204 anatomically positioned to facilitate implantation in the left acetabulum of the living being.

With reference to FIGS. 1A and 1B, like the first series of intermediate holes 105, a second series of intermediate holes 205 can be located between the third hole 202 and the fourth hole 204. Any of the third hole 202, the fourth hole 204 and/or one or more of the second series of intermediate holes 205 can form the second series of holes 200.

The second series of holes 200 can be positioned along the second arched line 210 (FIG. 2A, or approximated along element 240 in FIGS. 1A and 1B) that extends along the dome 12 of the shell 10 from the third hole 202 to the fourth hole 204. The second arched line 210 can correspond to an arch of bone 3 behind the left acetabulum 2 of the living being (e.g., left acetabulum is essentially the mirror image of the right acetabulum of FIG. 2A). The arch of bone 3 of the left acetabulum 2 can extend from a superior anterior portion 4 to an inferior posterior portion 6 of the left acetabulum 2 of the living being.

Because the second series of holes 200 can be arranged along the second arched line 210, and the second arched line 210 corresponds to the arch of bone 3 behind (e.g., proximate) a left acetabulum 2 of the living being, the second series of holes 200 can also correspond to the arch of bone 3 behind the left acetabulum 2 of the living being. This arrangement of holes 200 can provide anatomically positioned holes that the surgeon can rely on for alignment and fixation of the shell 10 to the bone of left acetabulum 2 and the surrounding bone. As in the first series of holes 100, in some examples, not all of the second series of holes 200 must be provided.

As shown in the example of FIGS. 1A, 1B and 2A, the first arched line 110 and the second arched line 210 can intersect one another (e.g., 110, 210 in FIG. 2A; and approximated by elongate markers 140, 240 in FIGS. 1A and 1B). This can result in the first series of holes 100 along the first arched line 110 and the second series of holes 200 along the second arched line 210 being mirror images of one another (e.g., generally mirror images of one another, subtle differences in specific living beings can result in variations between right and left sides). In some examples, and as shown in FIGS. 1A and 1B, one of the first series of holes 100 is the same as one of the second series of holes 200. In other examples, the first series of holes 100 and the second series of holes 200 do not intersect one another, and/or they do not share a common hole. This can occur, for example, when a shell is manufactured to fit a particular living being that has different hip bone anatomy between the right and left hip bones.

In some examples, the first and second series of holes 100, 200 do not intersect. For example, there can be situations where the shell 10 is not arranged for implantation into both the right and left acetabulum. For example, the shell 10 can be provided only for use with the right acetabulum, and the second series of holes 200 for the left acetabulum can be omitted. Vice versa, in some examples, the shell 10 can be provided only for use with the left acetabulum, and the first series of holes 100 for the right acetabulum 2 can be omitted.

The example shell 10 can also include other features in addition to the anatomically positioned holes. In some examples, one of the first series of holes 100 can be identified with a preferred hole marker(s) such as a first longest screw hole marker 146 (FIGS. 1A and 1B) that corresponds to a longest screw hole 106 location where the longest screw 136 can theoretically be placed superiorly in a right ilium 5 of a living being (e.g., screw 136 in FIG. 2A may appear shorter due to angle of insertion). Identifying the first longest screw hole 106 (FIGS. 1A and 1B) location can include identifying the hole location that corresponds to a bone location having preferred bone characteristics. This can be determined from the anatomic data. The preferred bone characteristics for the first longest screw hole 106 (e.g., preferred screw hole) can include, but are not limited to, the location where the longest screw can theoretically be placed superiorly in a right ilium 5 (FIG. 2A). Other locations can be provided with other markers having other preferred bone characteristics. Suitable markers can include markers to identify the sequence for inserting screws, markers to identify the left and right arcs or left and right holes, the pubis hole, and anatomical markings.

Similarly, one of the second series of holes 200 can be identified with a left longest screw hole marker 246 that corresponds to a location where a longest screw can theoretically be placed superiorly in a left ilium of the living being. As shown in FIGS. 1A and 1B, these first and second longest screw hole 106, 206 locations can be located inward of a common screw hole 108 location. To alert the surgeon to this potentially preferred screw hole location, the first longest screw hole marker 146 and a similar second longest screw hole marker 246 can be provided.

As perhaps most completely viewed in FIG. 1A, the previously mentioned first elongate marker 140, which can approximate the first arched line 110, will now be further described. The first elongate marker 140 can extend along the first arched line 110 (FIG. 2A) to help the surgeon align the shell 10 with the arch of bone 3 behind the acetabulum 2. Here, the first elongate marker 140 is shown as an engraved line extending between the holes of the first series of holes 100 and can extend to the first and second holes 102, 104. The first elongate marker 140 is merely one example of a marker. In the illustrated example, the first elongate marker 140 can extend between every hole in the first series of holes 100. In some examples, the first elongate marker 140 does not extend into the bearing taper 18 all the way to the first and second holes 102, 104. In other examples, the first elongate marker 140 does not extend between every hole in the first series of holes 100. The first elongate marker 140 shown in FIGS. 1A and 1B depict merely one example, a variety of other marker styles, designs, shapes, sizes, and methods of forming, can be provided and still be within the scope of this disclosure.

With reference to FIGS. 1A and 2A, in addition to the first series of holes 100 that can be provided along the first arched line 110, a first pubis hole 109 can be arranged to install a first pubis screw 139 (FIG. 2A) into a pubis 9 of the right acetabulum 2. For example, while the first hole 102 and the second hole 104 can be arranged to facilitate inserting screws 130 superiorly in an ilium 5 and inferiorly into an ischium 7, and the first series of intermediate holes 105 can facilitate inserting screws 130 (FIG. 2A) along the first arched line 110 between the first hole 102 and the second hole 104, the first pubis hole 109 can provide fixation to the bone in a different area which can lead to a secure and balanced implantation of the shell 10 in the right acetabulum 2.

To allow the shell to be implanted in both a right and left acetabulum. A corresponding second pubis hole (FIG. 1A, 209) can be arranged to install a second pubis screw (e.g., like 139 in FIG. 2A) into a pubis of the left acetabulum of the living being. For example, while the third hole 202 and the fourth hole 204 can be arranged to facilitate inserting screws 130 superiorly in an ilium 5 and inferiorly into an ischium 7 of the living being, and the second series of intermediate holes 105 can facilitate inserting screws along the second arched line 210 between the third hole 202 and the fourth hole 204, the second pubis hole 209, like the first pubis hole 109, can provide fixation to the bone in a different area which leads to a more secure and balanced implantation of the shell 10.

Example Method of Anatomically Positioning Screw Holes

Figure 3A:
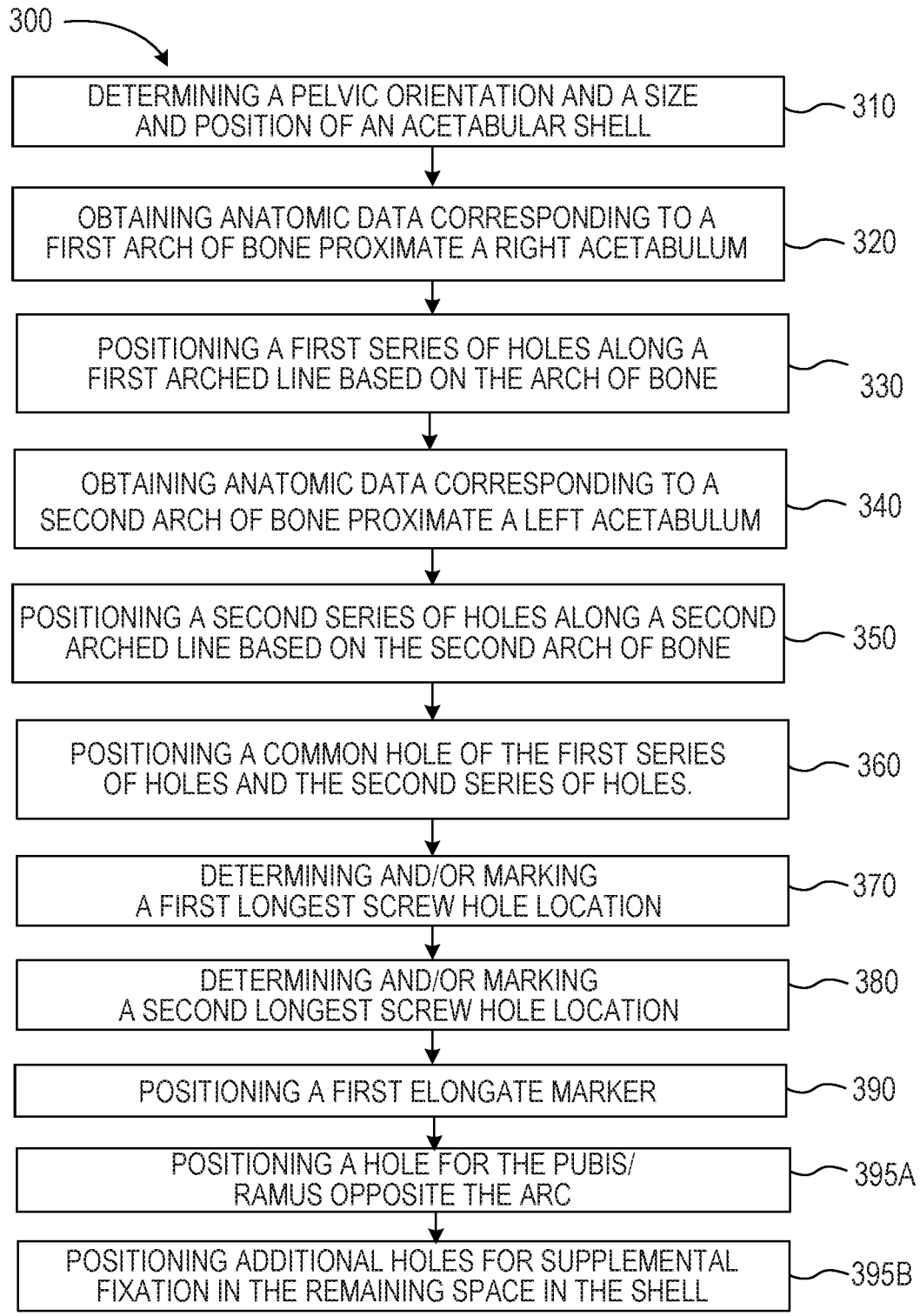
FIG. 3A is a flow chart illustrating an example method 300 of anatomically positioning holes in an illustrative shell, such as the shells of FIGS. 1A-1D or 2A-2G, in accordance with at least one example.

FIG. 3A is a flow chart illustrating an example method 300 of anatomically positioning screw holes 100 in an illustrative shell 10, such as the illustrative shell 10 of FIGS. 1A-1D described herein.

The example methods described herein are directed to anatomically positioning screw holes in a shell, such as a shell for a revision total hip arthroplasty. The methods will be described with reference to the example shell 10 of FIGS. 1A-1D and FIGS. 2A-2G. Any of the features and positioning described with reference to these figures, may be incorporated into the method steps. The example methods described herein are merely illustrative in nature. The example method can be practiced with other shells. The example methods are not limited to the steps specified herein. The methods can include fewer steps or additional method steps other than those described in this disclosure.

Step 310 of the method 300 can include determining a pelvic orientation and a size of a shell, such as a shell 10 previously described, having a hemispherical shaped dome 12 terminating at a face 14. The size of the shell 10 can correspond to a living being. The determining step 310 can be determined based on anatomic information. The anatomic information can be determined for a particular subset of a living being population. This anatomic information can be estimated based on, or derived from, predetermined or known measurements. The anatomic information can also be specific to a particular living being according to anatomic information specific to the particular living being, including information obtained during imaging of the particular living being.

Further, the step of determining the size of the shell can include using software to fit a best fit sphere to an acetabulum of a particular living being based off of imaging, such as a CT scan. The best fit sphere (e.g., diameter) can be offset by a set amount to simulate the amount of bone that would be removed in a preparation step, such as by reaming. In some examples, this can be referred to as the offset best fit diameter which can be used to determine the best shell size for the particular living being.

Step 320 can include obtaining anatomic data, such as arch anatomic data from an anatomic database. The arch anatomic data can correspond to an arch of bone 3 (FIG. 2A) proximate a right acetabulum 2 of the living being. For example, the arch of bone 3 can be described as the arch of bone 3 proximate the right acetabulum 2 extending from a superior anterior portion 4 to an inferior posterior portion 6 of the right acetabulum 2. The arch of bone 3 can be determined for a particular subset of a living being population. The arch anatomic data can be estimated based on, or derived from, predetermined or known measurements. The arch anatomic data can also be specific to a particular living being according to arch anatomic data, such as data obtained during imaging of the particular living being.

Step 330 can include positioning a first series of holes 100 along a first arched line 110 in the shell 10, the first arched line 110 corresponding to and based on the anatomic data for the arch of bone 3 proximate the right acetabulum 2 (FIG. 2A). The step 330 of positioning the first series of holes 100 in the shell 10 can include positioning a first hole 102 to accommodate a first screw 132. The first hole 102 can be positioned to be inserted superiorly into a right ilium 5 of the living being, however, in some embodiments, the first hole 102 can be positioned to be inserted into other parts of the acetabulum 2. Step 330 can also include positioning a second hole 104 in the shell 10 to accommodate a second screw 134 inserted inferiorly into a right ischium 7 of the living being. Like the first hole 102, the second hole 104 can also be positioned to be inserted into other parts of the acetabulum 2. In some examples, positioning the first and second holes 102, 104 can include positioning one or both of the first and second holes 102, 104 in the bearing taper 18 (e.g., hard bearing taper where a liner locks into a shell).

Figure 3B:
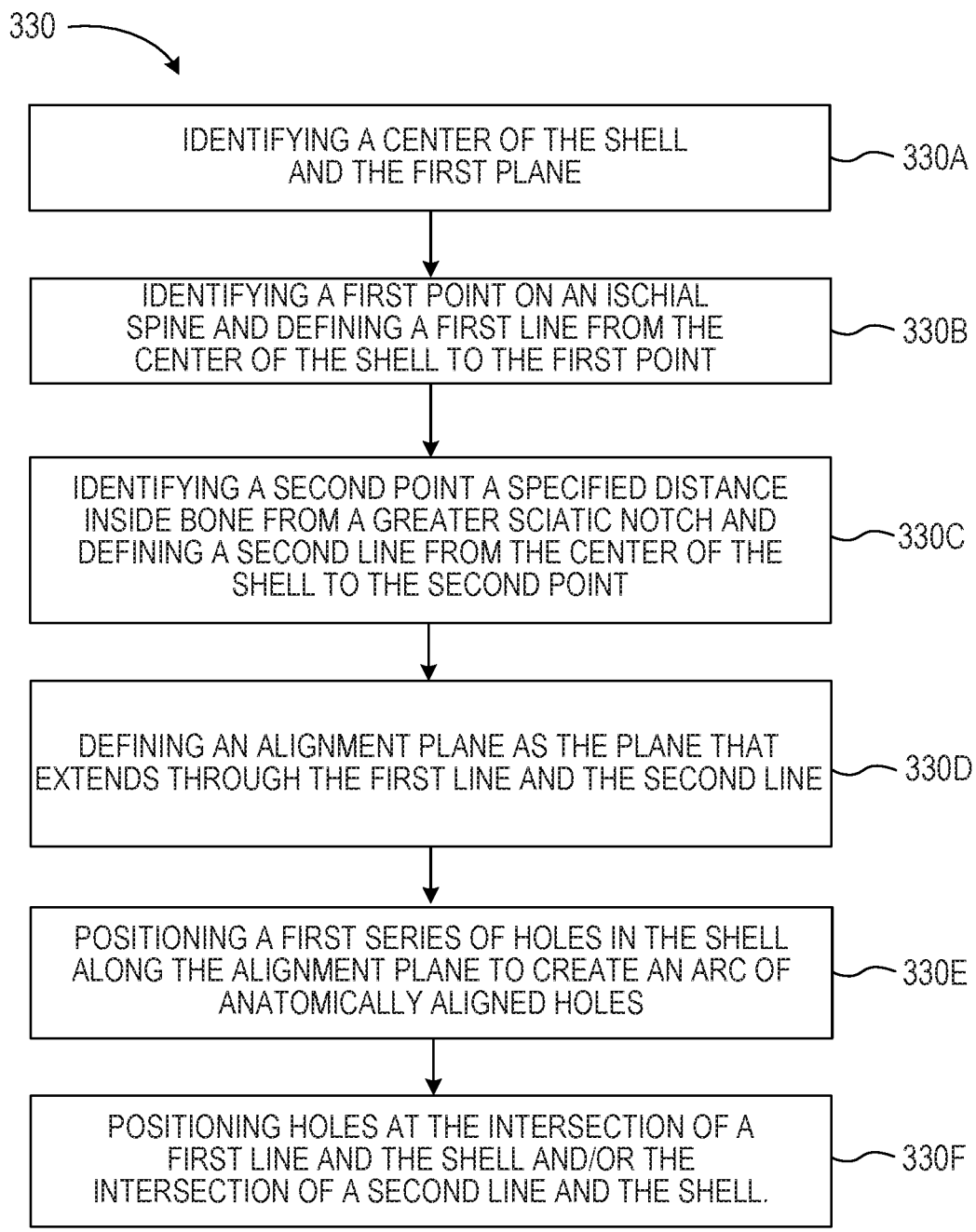
FIG. 3B is a flow chart illustrating method 330 (including sub-steps 330A-F) of anatomically positioning holes in an illustrative shell, such as the shell of FIGS. 1A-1D or 2A-2G. The method 330 can be used together, in part, or separately from the method 300 of FIG. 3A, in accordance with at least one example.

In some examples, the step 330 of the method of positioning a first series of holes 100 along a first arched line 110 in the shell 10 can further be described with respect to the example method 330, including sub-steps of the method 330A-330F illustrated in the flow chart of FIG. 3B, and with reference to the implanted shell 10 and other supporting figures of FIGS. 2A-2G.

In at least one example, step 330A can include identifying a center 17 of the shell 10 based on the selection of the proper anatomical position of the shell 10 that was performed in step 310. This provides a center location 17. For example, the inclination/anteversion can be about 40/20, or any other suitable inclination/anteversion. Step 330A can also include defining a first plane 11 that the shell face 14 is aligned to when the shell is properly positioned in step 330a. The first plane 11 can extend through the center 17 of the shell 10.

As shown in FIG. 2A, step 330B of FIG. 3B can include identifying a first point 27 on an ischial spine 24 and defining a first line (depicted as line with arrowhead) extending from the center 17 of the shell 10 through the first point 27. Also shown in FIG. 2A, similar step 330C can include identifying a second point 29 at a specified distance inside the hip bone 1 from a greater sciatic notch 8 aimed towards the iliac crest 25, and defining a second line (depicted as line with arrowhead) from the center 17 of the shell 10 to the second point 29. In some examples, the specified distance can be greater than 3 mm, between about 3 mm and 8 mm, about 5 mm, or any other suitable distance.

Step 330 D can include defining an alignment plane as the plane that extends through the first line and the second line. The first and second lines are shown with arrowheads in FIGS. 2A and 2B extending from the center 17 of the shell 10 outward towards first point 27 and second point 29. These two lines define the alignment plane. The alignment plane 13 is shown in and is perhaps best understood with reference to FIG. 2C. Step 330E can include positioning a first series of holes (e.g., any of holes 100 previously described with respect to FIGS. 1A and 1B) in the shell 10 along the alignment plane 13. The arc of anatomically aligned holes (first series of holes 100) can be defined where the alignment plane 13 intersects the shell 10 to create the first arched line 110. Step 330E can optionally include step 330F of positioning holes at the intersection of a first line and the shell and/or the second line and the shell 10.

Steps 340 and 350 can be similar to steps 320 and 330, but are directed to positioning holes in relation to a left acetabulum instead of a right acetabulum as described above. Step 340 can include obtaining arch anatomic data from the anatomic database, the arch anatomic data corresponding to an arch of bone 3 proximate a left acetabulum of the living being (e.g., mirror image of FIG. 2A), the arch of bone 3 proximate the left acetabulum extending from a superior anterior portion 4 to an inferior posterior portion 6 of the left acetabulum. Like step 320, the determination step 340 can be determined based on arch anatomic information obtained from an anatomic database. Again, the arch of bone 3 can be determined for the particular subset of a living being population or for the particular living being according to anatomic information, such as the information obtained during imaging of the particular living being.

Step 350 can include positioning a second series of holes 200 along a second arched line 210 in the shell 10, the second arched line 210 corresponding to and based on the anatomic data for the arch of bone proximate the left acetabulum. The step 350 of positioning the second series of holes 200 in the shell 10 can include positioning a third hole 202 to accommodate a third screw (e.g., like first screw 132 in FIG. 2A) inserted superiorly into a left ilium of the living being. Step 350 can also include positioning a fourth hole 204 in the shell 10 to accommodate a fourth screw (e.g., like second screw 134 in FIG. 2A) inserted inferiorly into a left ischium of the living being. In some examples, Step 340 can include some or all of the steps described with respect to FIG. 3B (e.g., steps 330A-330F), but applied to a left acetabulum.

In some examples, step 350 of positioning holes in relation to the left acetabulum can be described as providing a mirror image of the holes positioned in relation to the right acetabulum, or vice-versa. For example, positioning holes in relation to the left acetabulum can be completed first, followed by positioning holes in the right acetabulum, by the same method steps, or merely as a mirror image of the holes of the right acetabulum oriented in relation to the left acetabulum. In some examples, the holes are positioned based on data obtained for a particular living being and therefore the hole positions for the left acetabulum may not mirror the hole positions for the right acetabulum. This can occur due to variations in the right and left hip bones of the particular living being.

In examples where the first arched line 110 and the second arched line 210 intersect, step 360 can include positioning a common hole (e.g., FIG. 1A, 108/208) of the first series of holes 100 and the second series of holes 200. For example, the common hole can be arranged where the first arched line 110 and the second arched line 210 intersect. In some examples, positioning the common hole 108/208 can also include identifying the common hole 108/208 with a marker.

Step 370 can include determining which hole in the first series of holes 100 is a first longest screw hole 106 location, and identifying the first longest screw hole 106 with a first longest screw hole marker 146. The first longest screw hole 106 location corresponding to a location in the shell 10 where a longest screw can theoretically be placed superiorly in the right acetabulum 2 of the living being (FIG. 2A). Determining the first longest screw hole 106 location can include determining the location in the arch of bone 3 that has preferred bone characteristics. The preferred bone characteristics, can include, but are not limited to, the location in the shell 10 corresponding to where a longest screw can theoretically be placed superiorly in the right acetabulum 2 of the living being. The preferred bone characteristics can be obtained from any source(s) of anatomic data.

Similar to step 370, step 380 can include determining which hole in the second series of holes 200 is a second longest screw hole 206 location, and identifying the second longest screw hole 206 with a second longest screw hole marker 246. The second longest screw hole 206 location corresponding to a location in the shell 10 where a longest screw can theoretically be placed superiorly in the left acetabulum 2 of the living being (e.g., mirror image of FIG. 2A). Determining the second longest screw hole 206 location can include determining the location in the arch of bone 3 that has preferred bone characteristics. Again, the preferred bone characteristics can include, but are not limited to, the location in the shell 10 corresponding to where a longest screw can theoretically be placed superiorly in the left acetabulum of the living being. The preferred bone characteristics can include other characteristics and can be obtained from any source(s) of anatomic data.

Step 390, can include positioning a first elongate marker 140 (FIGS. 1A and 1B) extending along the first arched line 110 (FIG. 2A) to identify the first series of holes 100. In cases where the shell 10 includes both a first series of holes 100 and a second series of holes 200, step 390 can also include positioning a second elongate marker 240 (FIGS. 1A and 1B) extending along the second arched line 210 (FIG. 2A) to identify the second series of holes 200. The elongate markers 140, 240 can serve to highlight to the surgeon the first series of holes 100 that are provided for implantation into the right acetabulum 2 and the second series of holes 200 are provided for implantation into the left acetabulum (e.g., mirror image of FIG. 2A). The elongate markers 140, 240 can also serve to help with alignment of the shell 10 to the arch of bone 3.

Steps 395A and 395B can include positioning other holes in the shell 10. In some examples, step 395A can include positioning a pubis hole for attachment of the shell to the pubis (e.g., ramus) opposite from the first arched line 110. Step 395B can include positioning additional holes for supplemental fixation in the remaining space in the shell 10.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

VARIOUS NOTES AND EXAMPLES

To better illustrate the devices and methods disclosed herein, a non-limiting list of embodiments is provided herein.

Example 1 describes a method of anatomically positioning screw holes in an acetabular implant. In this example, the method can include determining a size of an acetabular shell, obtaining anatomic data, and positioning a series of holes on the acetabular shell. The determining a size of an acetabular shell having a hemispherical shaped dome and a rim can be based on anatomic information for a living being. Obtaining the anatomic data can include data defining an arch of bone behind an acetabulum of the living being. The arch of bone can extend from a superior anterior portion to an inferior posterior portion of the acetabulum. Positioning the first series of holes can include positioning the holes along a first arched line within the acetabular shell, where the first arched line can be determined based on the anatomic data for the arch of bone behind the acetabulum for the living being.

Example 2 includes the method of Example 1 and optionally includes that obtaining the anatomic data includes can include obtaining arch anatomic data for the living being.

Furthermore, positioning the first series of holes in the acetabular shell can include positioning a first hole to accommodate a first screw inserted superiorly into an ilium of the living being, and positioning a second hole to accommodate a second screw inserted inferiorly into an ischium of the living being.

Example 3 includes any one or more of Examples 1-2 and optionally includes that determining the size of the acetabular shell is based on anatomic information obtained from an anatomic database.

Example 4 includes any one or more of Examples 1-3 and optionally includes that the first arched line is positioned to follow the arch of bone behind the acetabulum for the living being.

Example 5 includes any one or more of Examples 1-4 and optionally includes that the first arched line is based on anatomic data representing a subset of a living being population that is obtained from an anatomic database.

Example 6 includes any one or more of Examples 1-5 and optionally includes that the first arched line is based on anatomic data of a particular living being.

Example 7 includes any one or more of Examples 1-6 optionally include determining which hole in the first series of holes is a longest screw hole location, the longest screw hole location corresponding to a location in the shell where a longest screw can theoretically be placed superiorly in the living being; and identifying the longest screw hole with a longest screw hole marker.

Example 8 includes Example 7 and optionally includes that determining the longest screw hole location includes determining a hole location in the arch of bone having preferred bone characteristics determined from the anatomic data.

Example 9 includes any one or more of Examples 1-8 and optionally includes that obtaining the anatomic data includes obtaining arch anatomic data for the arch of bone behind the acetabulum that corresponds to a right side of a body of a living being, the method further including: positioning a second series of holes in the acetabular shell, where positioning the second series of holes includes positioning the second series of holes along a second arched line in the shell, and the second arched line corresponds to and is based on an arch of bone behind a left acetabulum. The arch of bone behind the left acetabulum extending from a superior anterior portion to an inferior posterior portion of the left acetabulum, wherein the arch of bone behind the left acetabulum is based on the arch anatomic data.

Example 10 includes any one or more of Example 9 optionally includes wherein the first arched line and the second arched line intersect one another.

Example 11 includes any one or more of Examples 9-10 and optionally includes a first elongate marker extending along the first arched line to identify the first series of holes, and a second elongate marker extending along the second arched line to identify the second series of holes.

Example 12 includes any one or more of Examples 9-11 and optionally includes that positioning the first series of holes and positioning the second series of holes includes positioning one common hole belonging to both the first series of holes and the second series of holes.

Example 13 includes any one or more of Examples 9-12 and optionally includes wherein the first series of holes is a mirror image of the second series of holes.

Example 14 includes any one or more of Examples 9-13 and optionally includes that at least one of the first series of holes is located in a bearing taper proximate the rim of the shell, and at least one of the second series of holes is located in the bearing taper.

Example 15 describes a method of anatomically positioning screw holes in an acetabular implant. In this example, the method can include: determining a size of an acetabular shell having a hemispherical shaped dome terminating at a face. The size of the acetabular shell corresponding to a living being. The method can also include obtaining anatomic data from an anatomic database. The anatomic data obtained can correspond to an arch of bone proximate a right acetabulum of the living being. The arch of bone can be proximate the right acetabulum extending from a superior anterior portion to an inferior posterior portion of the right acetabulum. The method can also include positioning a first series of holes along a first arched line in the acetabular shell, the first arched line corresponding to and based on the anatomic data for the arch of bone proximate the right acetabulum. Obtaining anatomic data from the anatomic database can include obtaining the anatomic data corresponding to an arch of bone proximate a left acetabulum of the living being. The arch of bone proximate the left acetabulum extending from a superior anterior portion to an inferior posterior portion of the left acetabulum, and positioning a second series of holes along a second arched line in the acetabular shell, the second arched line corresponding to and based on the anatomic data for the arch of bone proximate the left acetabulum.

Example 16 can include Example 15 and optionally includes that the first arched line and second arched line are based on anatomic data representing a subset of a living being population that is obtained from an anatomic database.

Example 17 can include any one or more of Examples 15-16 and optionally includes that the first arched line and second arched line are based on anatomic data from a particular living being.

Example 18 can include any one or more of Examples 15-17 and optionally includes that positioning the first series of holes and positioning the second series of holes includes determining a location of a common hole of the first series of holes and the second series of holes, the common hole arranged where the first arched line and the second arched line intersect.

Example 19 can include any one or more of Examples 15-18 and optionally includes determining which one of the holes in the first series of holes is a longest screw hole location, the longest screw hole location corresponding to a location in the shell where a longest screw can theoretically be placed superiorly in the right acetabulum of the living being and identifying the longest screw hole location with a longest screw hole marker.

Example 20 an include any one or more of Examples 15-19 and optionally can include determining which one of the holes in the second series of holes is a second longest screw hole location. The second longest screw hole location can correspond to a location in the shell where a longest screw can theoretically be placed superiorly in the left acetabulum of the living being. Furthermore, the method can include identifying the second longest screw hole location with a second longest screw hole marker.

Example 21 can be an acetabular shell including a shell having a hemispherical shaped dome and a rim along a face of the shell. A bearing taper can be located proximate the rim and have a first hole and a second hole generally opposing one another in or adjacent the bearing taper. A first series of intermediate holes can be located along a first arched line that extends along the dome of the shell from the first hole to the second hole. The first hole, the second hole, and the first series of intermediate holes can correspond to an arch of bone behind a right acetabulum of a living being. The arch of bone of the right acetabulum can extend from a superior anterior portion to an inferior posterior portion of the right acetabulum of the living being. A third hole and a fourth hole can generally oppose one another in or adjacent the bearing taper. A second series of intermediate holes can be located along a second arched line that extends along the dome of the shell from the third hole to the fourth hole. The third hole, the fourth hole and the second series of intermediate holes can correspond to an arch of bone behind a left acetabulum of the living being. The arch of bone of the left acetabulum can extend from a superior anterior portion to an inferior posterior portion of the left acetabulum of the living being. The first arched line and the second arched line can intersect one another such that one of the first series of intermediate holes is the same as one of the second series of intermediate holes.

Example 22 can include Example 21 and optionally includes that the first and second arched lines are positioned at a down angle β of 40-75 degrees down from level with the face of the shell.

Example 23 can include any one or more of Examples 21-22 and optionally includes that one of the first series of intermediate holes is identified with a first longest screw hole marker that corresponds to a location where the longest screw can theoretically be placed superiorly in a right ilium of a living being. Furthermore, one of the second series of intermediate holes is identified with a left longest screw hole marker that corresponds to a location where the longest screw can theoretically be placed superiorly in a left ilium of the living being.

Example 24 can include any one or more of Examples 21-23 and optionally includes at least one pubis hole arranged to install a pubis screw into a pubis of the living being. The first hole and the second hole can be arranged to facilitate inserting screws superiorly in an ilium and inferiorly into an ischium of the living being, and the first series of intermediate holes facilitate inserting screws along the first arched line between the first hole and the second hole.

Example 25 can include of any one or more of Examples 21-24 and optionally includes that the first arched line and the second arched line are based on anatomic data representing a subset of a living being population that is obtained from an anatomic database.

Example 26 can include any one or more of Examples 21-25 optionally include wherein the first arched line and second arched line are based on anatomic data from a particular living being.

What is claimed is:

1. A method of anatomically positioning screw holes in an acetabular implant, the method comprising:
    determining, based on anatomic information for a living being, a size of an acetabular shell having a hemispherical shaped dome;
    obtaining anatomic data including data defining an arch of bone behind an acetabulum of the living being, the arch of bone extending from a superior anterior portion to an inferior posterior portion of the acetabulum; and
    positioning a first series of holes along a first arched line within the acetabular shell, the first arched line determined based on the anatomic data for the arch of bone behind the acetabulum for the living being,
    wherein the first arched line is positioned to follow the arch of bone behind the acetabulum for the living being,
    wherein a line extends along the first arched line to identify the first series of holes.

2. The method of claim 1, wherein obtaining the anatomic data includes obtaining arch anatomic data for the living being, and wherein positioning the first series of holes in the acetabular shell further comprises positioning a first hole to accommodate a first screw inserted superiorly into an ilium of the living being, and positioning a second hole to accommodate a second screw inserted inferiorly into an ischium of the living being.

3. The method of claim 1, wherein determining the size of the acetabular shell is based on anatomic information obtained from an anatomic database.

4. The method of claim 1, wherein the first arched line is based on anatomic data representing a subset of a living being population that is obtained from an anatomic database.

5. The method of claim 1, wherein the first arched line is based on anatomic data of a particular living being.

6. The method of claim 1 further comprising:
    determining which hole in the first series of holes is a longest screw hole location, the longest screw hole location corresponding to a location in the acetabular shell where a longest screw can theoretically be placed superiorly in the living being; and
    identifying the longest screw hole with a longest screw hole marker.

7. The method of claim 6, wherein determining the longest screw hole location includes determining a hole location in the arch of bone having preferred bone characteristics determined from the anatomic data.

8. The method of claim 1, wherein obtaining the anatomic data includes obtaining arch anatomic data for the arch of bone behind the acetabulum that corresponds to a right side of a body of a living being, the method further comprising:
    positioning a second series of holes in the acetabular shell, wherein positioning the second series of holes includes positioning the second series of holes along a second arched line in the acetabular shell, wherein the second arched line corresponds to and is based on an arch of bone behind a left acetabulum, the arch of bone behind the left acetabulum extending from a superior anterior portion to an inferior posterior portion of the left acetabulum, wherein the arch of bone behind the left acetabulum is based on the arch anatomic data.

9. The method of claim 8, wherein the first arched line and the second arched line intersect one another.

10. The method of claim 8, further comprising a first elongate marker extending along the first arched line to identify the first series of holes, and a second elongate marker extending along the second arched line to identify the second series of holes.

11. The method of claim 8, wherein positioning the first series of holes and positioning the second series of holes includes positioning one common hole belonging to both the first series of holes and the second series of holes.

12. The method of claim 8, wherein the first series of holes is a mirror image of the second series of holes.

13. The method of claim 8, wherein at least one of the first series of holes is located in a bearing taper proximate a rim of the shell, and wherein at least one of the second series of holes is located in the bearing taper.

14. A method of anatomically positioning screw holes in an acetabular implant, the method comprising:
    determining, based on anatomic information for a living being, a size of an acetabular shell having a hemispherical shaped dome;

obtaining anatomic data including data defining an arch of bone behind an acetabulum of the living being, the arch of bone extending from a superior anterior portion to an inferior posterior portion of the acetabulum; and positioning a first series of holes and a first elongate marker configured to identify the first series of holes along a first arched line within the acetabular shell, the first arched line determined based on the anatomic data for the arch of bone behind the acetabulum for the living being, wherein the first arched line is positioned to follow the arch of bone behind the acetabulum for the living being.

15. The method of claim 14, wherein obtaining the anatomic data includes obtaining arch anatomic data for the living being, and wherein positioning the first series of holes in the acetabular shell further comprises positioning a first hole to accommodate a first screw inserted superiorly into an ilium of the living being, and positioning a second hole to accommodate a second screw inserted inferiorly into an ischium of the living being.

16. The method of claim 14 further comprising:

determining which hole in the first series of holes is a longest screw hole location, the longest screw hole location corresponding to a location in the acetabular shell where a longest screw can theoretically be placed superiorly in the living being; and identifying the longest screw hole with a longest screw hole marker.

17. The method of claim 14, wherein at least one of the first series of holes is located in a bearing taper proximate a rim of the shell.

* * * * *